United States Patent [19]

Hearon et al.

[11] 4,337,202
[45] Jun. 29, 1982

[54] PROCESS OF MAKING L-GULONO GAMMA LACTONE

[75] Inventors: William M. Hearon, Portland, Oreg.; John F. Witte, Vancouver, Wash.

[73] Assignee: Boise Cascade Corporation, Boise, Id.

[21] Appl. No.: 254,925

[22] Filed: Apr. 16, 1981

[51] Int. Cl.$^3$ ............................................. C07D 307/32
[52] U.S. Cl. ..................................................... 549/314
[58] Field of Search ....................................... 260/343.6

[56] References Cited

FOREIGN PATENT DOCUMENTS 618907 5/1935 Fed. Rep. of Germany .
38-6462 5/1963 Japan .

OTHER PUBLICATIONS

Sharkov Angewandte Chemie, vol. 2, Aug. 1963, pp. 405–409.
Orten et al., Human Biochemistry 9th Edition, The C. V. Mosby Co., 1975.

Primary Examiner—Jane T. Fan
Attorney, Agent, or Firm—Eugene D. Farley

[57] ABSTRACT

L-gulono gamma lactone is made in a one-step process by the simultaneous hydrolysis and catalytic reduction with hydrogen in acid medium of polyglucuronic acid or a lower alkyl glucuronoside. A use statement—L gulono gamma lactone can be converted chemically or biologically to L-ascorbic acid (vitamin C).

10 Claims, No Drawings

PROCESS OF MAKING L-GULONO GAMMA LACTONE

BACKGROUND AND BRIEF STATEMENT OF THE INVENTION

This invention pertains to a process for making L-gulono gamma lactone, also known as gulonic acid lactone or gulonolactone, from polyglucuronic acid or a lower alkyl glucuronoside.

It pertains particularly to a process for making L-gulono gamma lactone from either cellulose or starch as the ultimate starting material for the synthetic procedure.

L-gulono gamma lactone is a material of great present and potential interest since it can be converted chemically or biologically to L-ascorbic acid (vitamin C). Thus if a synthetic route were to be provided for the production of L-gulonic acid from cellulose or starch, a route also would be provided for the ultimate conversion of these low-cost materials to vitamin C. Furthermore, this route would include fewer and less expensive synthetic operations than does the classis Reichstein synthesis which presently is used universally in all commercial vitamin C manufacturing procedures.

It accordingly is the general purpose of the present invention to provide an efficient, practical, low-cost process for producing L-gulono gamma lactone in high yield from either polyglucuronic acid, an easily obtained cellulose or starch derivative, or from a lower alkyl glucuronoside such as methyl glucuronoside, which is easily obtained from methyl glucoside which, in turn, is easily obtained from starch.

The prior art contains references to synthetic procedures of possible interest in carrying out this conversion.

Sharkov in Angew. Chem. Internat. Edit. Volume 2, pages 405–409 (1963) discloses a process for converting polysaccharides to the corresponding polyhydric alcohols. Thus cellulose is converted to sorbitol by hydrogenation at 160°–165° C., 60–80 atm. hydrogen pressure and a reaction time of 50–60 minutes in aqueous acid medium using a ruthenium catalyst. However, the use of cellulose as a starting material under the reaction conditions specified leads to the production of a polyhydric alcohol product, sorbitol, rather than the L-gulono gamma lactone product which is the product of the process disclosed herein.

German Pat. No. 618907 (Hoffman-LaRoche; May 13, 1934) discloses another procedure of interest.

In accordance with this procedure, polyhydroxy carbonic acids are prepared from the corresponding uronic acids by hydrogenating the latter in aqueous acid, under pressure and at elevated temperatures which do not essentially exceed 140° C. A nickel oxide-clay catalyst is specified. Specific procedures are given for converting mono-acetone-D-xyluronic to L-xylonic acid lactone and for converting alpha-D-methyl galacturoniside to L-galactonic acid. However, our attempts to apply the Hoffman-LaRoche procedure to the conversion of either polyglucuronic acid or methyl-glucuronoside to L-gulono gamma lactone resulted in failure because the nickel catalyst dissolved in the sulfuric acid reaction medium.

We now have discovered that L-gulono gamma lactone may be prepared easily and in high yields by the simple one-step procedure of simultaneously hydrolyzing and reducing polyglucuronic acid or an alkyl glucuroniside to the desired product.

The reduction is carried out with gaseous hydrogen in aqueous medium at a pH below about 4, at a reaction temperature of from about 100° to about 140° C., at a pressure of from about 600 to about 1500 psi in the presence of a periodic table Group VIII noble metal catalyst.

The reduction is carried out for a time sufficient to hydrolyze the glucosidic starting material to the corresponding free aldehyde (glucuronic acid) and to reduce the resulting free aldehyde to the desired L-gulono gamma lactone.

The possibility of obtaining successful results from this sequence is surprising, since the free aldehyde acide produced as an intermediate belongs to a class of compounds which de-carboxylate readily in acid solution. It therefore would be expected that it would lose carbon dioxide with resultant impossibility of subsequent conversion by reduction to L-gulono gamma lactone.

We have discovered, however, that under the reaction conditions stipulated herein, the starting materials are hydrolyzed slowly to the corresponding free aldehyde acid, i.e. to glucuronic acid. The latter, however, is reduced very rapidly to L-gulono gamma lactone. The reduction reaction accordingly takes place before the de-carboxylation occurs to any substantial extent. As a result, by the present method L-gulono gamma lactone may be obtained easily, economically and in many cases in yields in excess of 90% of the theoretical.

The reactions set forth herein are further unique in their selection of starting materials. Sharkov (supra) practices his described catalytic reduction in acid medium on cellulose as a starting material and obtains a polyhydric alcohol product. We employ either polyglucuronic acid, or an alkyl glucuronoside as starting materials. Our starting materials are characterized by the presence of a carboxyl group in their molecular structure. The complex cellulosic molecule is not characterized by the presence of free carboxyl groups.

In our synthetic procedure we have taken advantage of the fact that free carboxyl groups are not reduced under the catalytic hydrogenation conditions which we employ. Accordingly, we are enabled to produce the desired, commerically valuable, carboxyl-containing end product.

DESCRIPTION OF SPECIFIC EMBODIMENTS OF THE INVENTION

As indicated above, the herein described process for the synthesis of L-gulono gamma lactone comprises a one-step process in which an uronic acid glycoside, i.e. polyglucuronic acid or an alkyl glucuronoside is simultaneously hydrolyzed and catalytically reduced in aqueous acid medium to the corresponding aldonic acid, i.e. L-gulono gamma lactone. The following synthetic sequence, whereby either cellulose or starch may be converted to the desired product, illustrates the procedure.

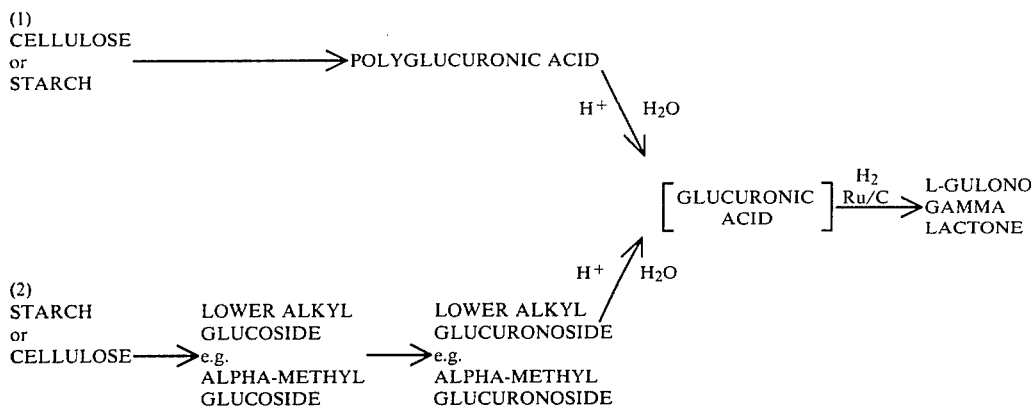

Where polyglucuronic acid is the starting material for our synthesis, it may be produced from cellulose in high yields by the method of:

W. O. Kenyon+E. C. Yackel J. Am. Chem. Soc. 64, 121 (1942);
W. O. Kenyon+C. C. Unruh ibid. 127

It may be produced from starch by the method of:

R. W. Kerr, J. Am. Chem. Soc. 72, 816 (1950).

Where a lower alkyl glucuronoside having from 1–5 carbon atoms in the alkyl group, e.g. alpha-methyl glucuronoside, is the starting material for our synthesis, it may be made from the corresponding alkyl glucosides by the methods of:

Barker, Bourne & Stacey, Chem. and Ind. 8970 (195);
Heynes & Paulson Agnew. Chem. 69 600 (1957).

The lower alkyl glucosides may be produced from cellulose by the procedure set forth by Irvine and Santar in:

J. Chem. Soc. London 117; 1489 (1920).

They may also be produced from starch by the method of:

E. Fischer Ber. 28 1145 1895.

In carrying out the procedure of our invention, the uronic acid glycoside starting material is hydrolyzed and reduced in a one-step reaction to form L-gulonic acid, which is isolated as its gamma lactone. As noted above, the conversion takes place in two stages. The first, i.e. the hydrolysis of the uronic acid glycoside to the free aldehyde acid, occurs relatively slowly under the conditions of the reaction. The second, i.e. the reduction of the aldehyde group of the aldehyde acid resulting from the hydrolysis, occurs very rapidly—before decarboxylation of the aldehyde acid can occur.

The conditions of reaction are critical in achieving this result. The required conditions are: reduction with gaseous hydrogen in acid aqueous medium using as critical catalysts the noble metals of Group VIII of the periodic table: i.e. platinum, palladium, ruthenium, rhodium and osmium. Other well-known hydrogenation catalysts, for example elemental nickel, are totally ineffective in achieving the desired result.

The procedure is carried out in conventional hydrogenation equipment. Hydrogen is introduced into the reaction vessel, which is maintained at from about 100° to about 140° C., preferably 120° to 135° C., and a pressure of from about 600 to about 1500 psi. The catalyst is used in the form of small particles deposited on a suitable carrier, for example particles of carbon or selected clays. In a typical case, from about 0.1 to about 1.0, preferably about 0.5%, catalyst is employed, based on the glycosidic starting material.

In carrying out the reaction, the glycoside is suspended or dissolved in aqueous medium having a pH value of less than about 4. Preferably the pH of the reaction mixture is adjusted to a value of less than about 1.6 by the addition of a non-oxidizing mineral acid. Preferred acids are the strong mineral acids, in particular sulfuric acid, hydrochloric acid, and phosphoric acid. In some cases the acidity of the glucuronoside starting material suffices to establish the desired pH level.

The reaction is carried on until an analysis of an aliquot portion shows that the starting material has disappeared. The reaction mixture is cooled to room temperature and filtered to separate the catalyst. The filtrate then is neutralized with a suitable basic material, filtered, if necessary, to remove any precipitate produced by the neutralization step, and evaporated under reduced pressure to the concentration desired for crystallizing the product.

The crystallization step is accomplished by adding a suitable hot solvent in the predetermined amount, cooling, and filtering off the crystallized product. Depending in particular upon the purity of the starting material, yields in excess of 90% of the theoretical may be obtained. The product, if isolated, is obtained in the form of its gamma lactone.

The process of our invention is further illustrated by the following examples.

EXAMPLE I

This example illustrates the preparation of L-gulono gamma lactone from polyglucuronic acid.

A suspension of 25.0 g. (0.14 mol) of polyglucuronic acid (24.9% carboxyl content) in 1 l. of 1% sulfuric acid was stirred in an atmosphere of hydrogen (1000 p.s.i.g) in an autoclave with 1.0 g. of 5% ruthenium-on-carbon catalyst at 130° C. for 2 hours. The polyglucuronic acid was obtained by the nitrogen tetroxide oxidation of cellulose by the method of Kenyon et al, supra.

At the end of two hours the reaction mixture was cooled to room temperature. The contents of the autoclave were filtered from the catalyst. The filtrate was neutralized with barium acetate to pH 1.9 and the precipitated barium sulfate filtered off.

The filtrate was evaporated under reduced pressure to a thick syrup. The syrup was dissolved in 200 ml. of glacial acetic acid. Pure L-gulono-gamma-lactone crystallized and was isolated by filtration. The yield was 12.6 grams, or 45% of the theoretical.

EXAMPLE II

This example illustrates the application of a palladium catalyst to the process of the invention.

The procedure of Example I was repeated, with the exception that a 5% palladium-on-carbon catalyst was substituted for the ruthenium-on-carbon catalyst of Example I. Also, the sulfuric acid component of the reaction mixture of Example I was omitted. The desired pH level of 1.6 was established and maintained by autohydrolysis.

Upon working up the reaction mixture and crystallizing the reaction product, L-gulono-gamma-lactone again was obtained, in approximately 45% yield.

EXAMPLE III

This example illustrates the production of L-gulono-gamma lactone from alpha-methylglucuronoside.

The alpha-methylglucuronoside starting material was obtained by the platinum-catalyzed oxygen oxidation of 120.3 grams of alpha-methylglucoside to 25% completion.

0.155 mol. of this material in one liter of 1% sulfuric acid was stirred under hydrogen (700 p.s.i.g.) at 120° C. for two hours with 1.0 gram 5% ruthenium-on-carbon catalyst in an autoclave. The reaction mixture was worked up in the manner set forth in Example I to yield 21.5 grams of pure L-gulono-gamma-lactone. This represents a yield of 90% of the theoretical.

EXAMPLE IV

The procedure of Example III is followed using in place of the ruthenium catalyst, in separate runs, a corresponding palladium catalyst, rhodium catalyst, and osmium catalyst. In each case the desired L-gulono gamma lactone product is obtained in good yields.

EXAMPLE V

This example illustrates the inapplicability of catalysts other than the group 8 of the periodic table noble metal catalysts for the purposes of the present invention.

A suspension of 20.0 g. of polyglucuronic acid (celluronic acid) in 1,000 ml. water (pH 1.6) was stirred in an autoclave under 1000 p.s.i. hydrogen with 2.0 g. Raney nickel catalyst at 125°–133° C. for three hours. At the end of this time the reaction mixture was cooled to room temperature. The contents of the autoclave were filtered. The pale green filtrate was acidified to pH 1.6 with 2 N sulfuric acid and analyzed for L-gulono-gamma-lactone. None of the desired product was isolatable, or even detectable, in the reaction mixture.

Having thus described our invention in preferred embodiments, we claim:

1. The one-step process of making L-gulono gamma lactone which comprises reacting a uronic acid glycoside of the class consisting of polyglucuronic acid and a lower alkyl glucuronoside having from 1–5 carbon atoms in the alkyl group
   with hydrogen in an aqueous medium at a pH below about 4 at a reaction temperature of from about 120° to about 140° C. at a pressure of from about 600 to about 1500 p.s.i. in the presence of a periodic table Group VIII noble metal catalyst comprises at least one member of the group consisting of platinum, palladium, ruthenium, rhodium and osmium
   for a time sufficent to hydrolyze the glycoside to the corresponding free aldehyde, and to reduce the resulting free aldehyde to L-gulono gamma lactone.
2. The process of claim 1 wherein the uronic acid glycoside comprises polyglucuronic acid.
3. The process of claim 1 wherein the uronic acid glycoside comprises a lower alkyl glucuronoside.
4. The process of claim 1 wherein the uronic acid glycoside comprises alpha-methyl glucoside.
5. The process of claim 1 wherein the reaction temperature is from about 120° to 135° C.
6. The process of claim 1 wherein the pH of the aqueous medium is below about 1.6.
7. The process of claim 1 wherein the catalyst comprises small particles of ruthenium.
8. The process of claim 1 wherein the catalyst comprises small particles of platinum.
9. The process of claim 1 wherein the catalyst comprises small particles of palladium.
10. The process of claim 1 wherein the catalyst comprises small particles of rhodium.

* * * * *